United States Patent
Lafontaine

(12) 
(10) Patent No.: US 6,343,605 B1
(45) Date of Patent: Feb. 5, 2002

(54) PERCUTANEOUS TRANSLUMINAL MYOCARDIAL IMPLANTATION DEVICE AND METHOD

(75) Inventor: Daniel M. Lafontaine, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/634,112

(22) Filed: Aug. 8, 2000

(51) Int. Cl.$^7$ ............................................. A61B 19/00
(52) U.S. Cl. ..................... 128/898; 623/3.1; 623/3.12; 606/16
(58) Field of Search .................. 128/898; 600/562, 600/16, 37; 623/3

(56) References Cited

U.S. PATENT DOCUMENTS

| | | | |
|---|---|---|---|
| 4,192,293 A | 3/1980 | Asrican | 128/1 D |
| 4,261,342 A | 4/1981 | Duo | 128/1 R |
| 4,372,293 A | 2/1983 | Vijil-Rosales | 128/1 R |
| 4,409,974 A | 10/1983 | Freedland | 128/92 B |
| 4,536,893 A | 8/1985 | Parravicini | 623/3 |

(List continued on next page.)

FOREIGN PATENT DOCUMENTS

| | | |
|---|---|---|
| DE | 36 14 292 C1 | 11/1987 |
| DE | 42 34 127 A1 | 5/1994 |
| EP | 0 583 012 A1 | 2/1994 |
| WO | WO 91/19465 | 12/1991 |
| WO | WO 95/06447 | 3/1995 |
| WO | WO 95/16476 | 6/1995 |
| WO | WO 96/04852 | 2/1996 |
| WO | WO 96/40356 | 12/1996 |
| WO | WO 97/24101 | 7/1997 |
| WO | WO 98/03213 | 1/1998 |
| WO | WO 98/18393 | 5/1998 |
| WO | WO 98/26738 | 6/1998 |
| WO | WO 98/32382 | 7/1998 |
| WO | WO 99/13777 | 3/1999 |
| WO | WO 99/44534 | 9/1999 |

OTHER PUBLICATIONS

Carpentier et al., "Myocardial Substitution with a Stimulated Skeletal Muscle: First Successful Clinical Case," *The Lancet,* Boston, Mass. and London, vol. 1, No. 8439, Letter to the Editor, May 25, 1985, p. 1267.

Ianuzzo et al., "Preservation of the Latissimus Dorsi Muscle During Cardiomyoplasty Surgery," *J. Card. Surg.,* vII(2):99–108 (1996).

(List continued on next page.)

*Primary Examiner*—Corrine McDermott
*Assistant Examiner*—Urmi Chattopadhyay
(74) *Attorney, Agent, or Firm*—Crompton Seager & Tufte LLC

(57) ABSTRACT

Devices and methods for increasing the volume of blood pumped by a heart muscle are disclosed. A therapeutic catheter in accordance with the present invention may comprise an elongate shaft having a proximal end, a distal end, and a lumen extending through at least a portion thereof. The therapeutic catheter may further include a cutter having a cutter lumen fixed to the distal end of the elongate shaft, and a mooring shaft slidingly disposed within the lumen of the elongate shaft. A method in accordance with the present invention may include the steps of engaging a muscle of a donor site with a portion of the mooring shaft, penetrating the muscle of the donor site with the cutter to form a muscle tendril, withdrawing the muscle tendril from the muscle of the donee site, positioning the distal end of the therapeutic catheter proximate a pit defined by the tissue of a donee site, inserting the muscle tendril into the tissue of the donee site, and disengaging the mooring shaft from the muscle tendril.

11 Claims, 13 Drawing Sheets

U.S. PATENT DOCUMENTS

| | | | | |
|---|---|---|---|---|
| 4,666,443 A | * | 5/1987 | Portner | 623/3 |
| 4,813,952 A | * | 3/1989 | Khalafalla | 623/3 |
| 4,936,857 A | | 6/1990 | Kulik | 623/3 |
| 4,944,753 A | | 7/1990 | Burgess et al. | 623/16 |
| 4,960,424 A | | 10/1990 | Grooters | 623/2 |
| 4,997,431 A | | 3/1991 | Isner et al. | 606/15 |
| 5,098,442 A | * | 3/1992 | Grandjean | 623/3 |
| 5,106,386 A | | 4/1992 | Isner et al. | 606/15 |
| 5,131,905 A | | 7/1992 | Grooters | 600/16 |
| RE34,021 E | | 8/1992 | Mueller et al. | 604/51 |
| 5,169,381 A | | 12/1992 | Snyders | 600/16 |
| 5,192,314 A | * | 3/1993 | Daskalakis | 623/3 |
| 5,250,049 A | | 10/1993 | Michael | 606/72 |
| 5,284,488 A | | 2/1994 | Sideris | 606/213 |
| 5,385,528 A | | 1/1995 | Wilk | 600/18 |
| 5,433,727 A | | 7/1995 | Sideris | 606/213 |
| 5,450,860 A | | 9/1995 | O'Connor | 128/898 |
| 5,452,733 A | | 9/1995 | Sterman et al. | 128/898 |
| 5,458,574 A | | 10/1995 | Machold et al. | 604/101 |
| 5,496,305 A | | 3/1996 | Kittrell et al. | 606/15 |
| 5,509,428 A | | 4/1996 | Dunlop | 128/898 |
| 5,533,958 A | | 7/1996 | Wilk | 600/18 |
| 5,571,215 A | | 11/1996 | Sterman et al. | 623/66 |
| 5,584,803 A | | 12/1996 | Stevens et al. | 604/4 |
| 5,593,424 A | | 1/1997 | Northrup, III | 606/232 |
| 5,682,906 A | | 11/1997 | Sterman et al. | 128/898 |
| 5,702,343 A | | 12/1997 | Alferness | 600/37 |
| 5,718,725 A | | 2/1998 | Sterman et al. | 623/2 |
| 5,758,664 A | * | 6/1998 | Campbell | 128/898 |
| 5,800,334 A | | 9/1998 | Wilk | 600/18 |
| 5,800,528 A | | 9/1998 | Lederman et al. | 623/3 |
| 5,814,097 A | | 9/1998 | Sterman et al. | 623/2 |
| 5,849,005 A | | 12/1998 | Garrison et al. | 606/1 |
| 5,855,614 A | | 1/1999 | Stevens et al. | 623/11 |
| 5,865,791 A | | 2/1999 | Whayne et al. | 604/49 |
| 5,957,977 A | | 9/1999 | Melvin | 623/3 |
| 5,984,857 A | | 11/1999 | Buck et al. | 600/16 |
| 6,045,497 A | | 4/2000 | Schweich, Jr. et al. | 600/16 |
| 6,059,715 A | * | 5/2000 | Schweich, Jr. | 600/16 |
| 6,110,100 A | * | 8/2000 | Talpade | 600/37 |

OTHER PUBLICATIONS

Chachques et al., "Latissimus Dorsi Dynamic Cardiomyoplasty," *Ann. Thorac. Surg.,* 1989:47:600–604.

Moreira et al., "Latissimus Dorsi Cardiomyoplasty in the Treatment of Patients with Dilated Cardiomyopathy," *Circulation,* 82(5suppl.): IV 257–63 (Nov. 1990).

Lucas et al., "Long–Term Follow–Up (12 to 35 Weeks) After Dynamic Cardiomyoplasty," *JACC,* vol. 22, No. 3, Sep. 1993:758–67.

Batista et al., "Partial Left Ventriculectomy to Improve Left Ventricular Function in End–Stage Heart Disease," *J. Card. Surg.,* 1996:11:96–98.

Kormos et al., "Experience with Univentricular Support in Mortally Ill Cardiac Transplant Candidates," *Ann. Thorac. Surg.,* 1990:49:261–71.

Sakakibara et al., "A Muscle Powered Cardiac Assist Device for Right Ventricular Support: Total Assist or Partial Assist?," *Trans. Am.Soc. Artif. Intern. Organs,* vol. XXXVI, 1990, pp. 372–375.

Farrar et al., "A New Skeletal Muscle Linear–Pull Energy Convertor as a Power Source for Prosthetic Support Devices," *The Journal of Heart & Lung Transplantation,* vol. 11, No. 4, part 2, Jul./Aug. 1992, pp. S341–350.

Bocchi et al., "Clinical Outcome after Surgical Remodeling of Left Ventricle in Candidates to Heart Transplantation with Idiopathic Dilated Cardiomypathy—Short Term Results," *Supplement to Circulation,* supp. II, vol. 96, No. 9, Nov. 4, 1997, pp. II–165–72.

Dickstein et al., "Heart Reduction Surgery: An Analysis of the Impact on Cardiac Function," *The Journal of Thoracic and Cardiovascular Surgery,* vol. 113, No. 6, Jun. 1997, pp. 1032–40.

Edie, M. D. et al., "Surgical repair of single ventricle," *The Journal of Thoracic and Cardiovascular Surgery,* vol. 66, No. 3, Sep., 1973, pp. 350–360.

Lev, M. D., et al., "Single (Primitive) Ventricle," *Circulation,* vol. 39, May, 1969, pp. 577–591.

Shumacker, "Cardiac Aneurysms," *The Evolution of Cardiac Surgery,* 1992, pp. 159–165.

Feldt, M. D., "Current status of the septation procedure for univentricular heart," *The Journal of Thoracic and Cardiovascular Surgery,* vol. 82, No. 1, Jul., 1981, pp. 93–97.

Doty, M. D. "Septation of the univentricular heart," *The Journal of Thoracic and Cardiovascular Surgery,* vol. 78, No. 3, Sep., 1979, pp. 423–430.

Savage, M. D., "Repair of left ventricular aneurysm," *The Journal of Thoracic and Cardiovascular Surgery,* vol. 104, No. 3, Sep., 1992, pp. 752–762.

McCarthy et al., "Early Results with Partial Left Ventriculectomy," *The Journal or Thoracic and Cardiovascular Surgery,* vol. 114, No. 5, Nov. 1997, pp. 755–765.

Cox, "Left Ventricular Aneurysms: Pathophysiologic Observations and Standard Resection," *Seminars in Thoracic and Cardiovascular Surgery,* vol. 9, No. 2, Apr., 1997, pp. 113–122.

Melvin, "Ventricular Radius Reduction Without Resection: A Computational Analysis," (abstract) *ASAIO Journal,* 45:160–165, 1999.

Batista et al., "Partial Left Ventriculectomy to Improve Left Venticular Function in End–Stage Heart Disease," *J. Card. Surg.,* 1996:11:96–98.

http://www.bioheartinc.com/publications/regeneration.html download Oct. 18, 2000.

http://www.bioheartic.com/biomicro.html Oct. 18, 2000.

Melvin et al., "Cardiomyoctes can be generated from marrow stormal cells in vitro", *The Journal of Clinical Investigation,* vol. 13, No. 5, pp. 697–705 (Mar. 1999).

Taylor et al., "Regerenating functional myocardium: Improved performance after skeletal myoblast transplantation," *Nature Medicine,* vol. 4, No. 8, pp. 929–33 (Aug. 1998).

Arnold I. Caplan, PhD, "The Mesengenic Process", *Clinics in Plastic Surgery,* vol. 21, No. 3, pp. 429–435 (Jul. 1994).

Ianuzzo et al., "On Preconditioning of Skeletal Muscle: Application to Dynamic Cardiomyoplasty," Invited Commentary, *J. Card. Surg.,* vII(2):109–110 (1996).

* cited by examiner

PERCUTANEOUS TRANSLUMINAL MYOCARDIAL IMPLANTATION DEVICE AND METHOD

FIELD OF THE INVENTION

The present invention relates generally to devices and methods for increasing the blood pumping efficiency of a heart muscle. More particularly, the present invention relates to devices and methods for treating a heart including one or more areas of non-contracting myocardial tissue that are causing low output ejection fraction.

BACKGROUND OF THE INVENTION

The blood pumping action of the heart muscle is critical to sustaining the life of a patient. One condition that is likely to reduce the blood pumping efficiency of the heart muscle is ventricular dilation. When ventricular dilation occurs a ventricle chamber (commonly the left ventricular chamber) becomes enlarged. As the chamber becomes enlarged, the internal surface area of the chamber increases rapidly. Blood flowing within the heart applies pressure to the internal surface of the heart chamber. Because the blood applies pressure inside the heart chamber across an increased surface area, the force which must be produced by the heart in order to pump blood also increases. In many cases, the cardiac disease which caused the ventricular dilation also limits the ability of the heart muscle to produce the increased force required to efficiently pump blood. In many cases, the dilation of the heart chamber becomes progressively worse, and the blood pumping efficiency of the heart muscle progressively declines. Ultimately, ventricular dilation may result in heart failure.

In order for the heart to function properly the tissues of the heart muscle must be continuously supplied and re-supplied with oxygen. To receive an adequate supply of oxygen, the heart muscle must be well perfused with blood. If the flow of blood to a portion of the heart muscle is interrupted or diminished, that portion of the heart muscle may stop contributing to the blood pumping action of the heart muscle.

In a healthy heart, blood perfusion is accomplished with a system of blood vessels and capillaries. However, it is common for the blood vessels to become occluded (blocked) or stenotic (narrowed). A stenosis may be formed by an atheroma that is typically a harder, calcified substance that forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique that may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques that treat individual lesions are not practical other techniques of improving the oxygenation of myocardial tissue may be utilized. One technique of improving the oxygenation of myocardial tissue is known as percutaneous myocardial revascularization (PMR). A PMR procedure generally involves the creation of holes, craters or channels directly into the myocardium of the heart. PMR was inspired in part by observations that reptilian heart muscles are supplied with oxygen primarily by blood perfusing directly from within heart chambers to the heart muscle. This contrasts with the human heart, which is supplied by coronary vessels receiving blood from the aorta. Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenisis. In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

SUMMARY OF THE INVENTION

The present invention relates generally to devices and methods for increasing the volume of blood pumped by a heart muscle. More particularly, the present invention relates to devices and methods for treating a heart including one or more areas of non-contracting myocardial tissue that are causing low output ejection fraction. A therapeutic catheter in accordance with the present invention includes a distal end, a proximal end, and an elongate shaft defining a lumen. A hub is disposed about the elongate shaft proximate its proximal end and a cutter is fixed to the elongate shaft proximate its distal end. The cutter includes a distal edge and a cutter lumen.

The therapeutic catheter also includes a mooring member disposed at a distal end of a mooring shaft. In a preferred embodiment, the mooring shaft is slidingly disposed within the lumen of the elongate shaft and cutter lumen of the cutter. A knob is fixed to a proximal end of the mooring shaft. In a preferred embodiment, the knob is adapted to be rotated by the fingers of a physician. In this preferred embodiment, the rotary motion of the knob is transferred to the mooring member via the mooring shaft.

A trocar in accordance with the present invention includes a body defining a trocar lumen. The body of the trocar includes a flange, a penetrating portion, a distal end, and a proximal end. A proximal aperture of the trocar is in fluid communication with the trocar lumen. In a preferred embodiment, the trocar lumen of the trocar is adapted to receive the therapeutic catheter. In a preferred method in accordance with the present invention, the distal end of the therapeutic catheter is inserted into the trocar lumen through the proximal aperture.

A guide catheter in accordance with the present invention includes an elongate tubular member defining a central lumen. A plurality of moorings are disposed proximate a distal end of the guide catheter. In one method in accordance with the present invention, the moorings may be utilized to retain the distal end of the guide catheter proximate a donee site. In a preferred embodiment, each mooring comprises a vacuum orifice. In this preferred embodiment, each vacuum orifice is in fluid communication with a vacuum lumen defined by the elongate tubular member of the guide catheter.

Other embodiments of the moorings are possible without deviating from the spirit or scope of the present invention. For example, each mooring may be comprised of an elongate wire with a helix disposed proximate its distal end. The helical end of the elongate wire may be "threaded" into the tissue proximate the donee site by rotating the wire. Additional examples, of moorings that may be appropriate in some applications include hooks and barbs.

A method in accordance with the present invention may include the step of penetrating the skin of a patient with a trocar near a donor site. In a preferred method, the donor site includes muscle tissue. Examples of donor sites that may be suitable in some applications include arms and legs.

The distal end of a therapeutic catheter in accordance with the present invention may be inserted through a proximal orifice of the trocar. The therapeutic catheter may be urged forward through a lumen of the therapeutic catheter until a cutter of the therapeutic catheter contacts muscle tissue proximate the donor site. The mooring shaft may be urged forward within the lumen of the therapeutic catheter by applying a pushing force to the knob disposed at the proximal end of the mooring shaft. The mooring shaft may be urged forward until the mooring member of the therapeutic catheter contacts the muscle tissue of the donor site. The mooring member of the therapeutic catheter may be coupled to the muscle tissue of the donor site. In a preferred method, the mooring member is fixed to the muscle tissue by threading it into the tissue. In this preferred method, the mooring member may be rotated by applying a rotational force to the knob fixed to the proximal end of the mooring shaft.

A tendril of muscle tissue may be cut from the donor site. In a preferred method, the step of cutting the muscle tendril includes the step of urging a cutter into the muscle tissue of the donor site. The therapeutic catheter may be withdrawn from the donor site with the tendril of muscle tissue disposed within the cutter lumen.

Methods in accordance with the present invention have been envisioned in which a pulling force is applied to the knob disposed at the end of the mooring shaft. The step of pulling on the mooring shaft may be utilized to urge the muscle tendril proximally. Methods in accordance with the present invention have been envisioned in which one or more muscle tendrils are pulled into the lumen of the therapeutic catheter.

A guide catheter may be introduced into the vasculature of the patient. The guide catheter is urged forward until its distal tip is proximate a desired donee site. In a preferred method, the distal tip is urged forward until it is disposed within the heart of the patient.

Once the distal end of the sheath is positioned proximate a desire donee site, the guide catheter may be advanced so that its distal end contacts the tissue proximate the donee site. The moorings of the guide catheter may then be activated to stabilize the distal end of the guide catheter. In one embodiment of the present invention, each mooring comprises of a vacuum orifice in fluid communication with a vacuum lumen. In one method in accordance with the present invention, the moorings of the guide catheter are activated by applying vacuum from a vacuum source to the vacuum orifices via the vacuum lumens.

A pit or channel may be created in the tissue of the donee site proximate the distal end of the guide catheter. A number of methods are known in the art for creating channels or pits in body tissue. Examples of methods that may be suitable in some applications include mechanical cutting and burning by exposure to electromagnetic energy. Examples of types of electromagnetic energy that may be suitable in some applications include radio frequency energy and LASER light. A pit forming catheter may be utilized to remove material proximate the distal end of the guide catheter. A process in accordance with the present invention may include the step of inserting a pit forming catheter into the lumen of the guide catheter. The pit forming catheter may be urged forward until its distal end is proximate the distal end of the guide catheter. A pit forming member disposed proximate the distal end of the pit forming catheter may be utilized to form a pit in the tissue proximate the donee site. Examples of pit forming members that may be suitable in some applications include knives, tomes, optical fibers, and electrodes. The pit forming catheter may be withdrawn from the lumen of the guide catheter.

The distal end of a therapeutic catheter may be inserted into the proximal port of the guide catheter. The therapeutic catheter may be urged forward within the lumen of the guide catheter until the distal portion of the therapeutic catheter is disposed proximate the pit or channel in the tissue of the donee site. The muscle tendril may then be urged into the pit or channel in the tissue of the donee site. In a preferred method, the muscle tendril is urged forward by applying a pushing force on the knob fixed to the proximal end of the mooring shaft.

While the muscle tendril is disposed within the pit or channel in the tissue of the donee site, the muscle tendril may be, preferably, fixed in place with an anchor member. Various anchor members may be utilized without deviating from the spirit and scope of the present invention. Examples of anchor members include sutures, staples, cauterized areas of tissue, adhesive bonds, cork screws, wire loops, sleeves, barbs, and hooks. After the muscle tendril has been positioned in the pit or channel and preferably, anchored, the mooring member of the therapeutic catheter may be disengaged from the muscle tendril. In a preferred method, the mooring is disengaged from the muscle tendril by applying a rotational force to the knob fixed to the proximal end of the mooring shaft.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
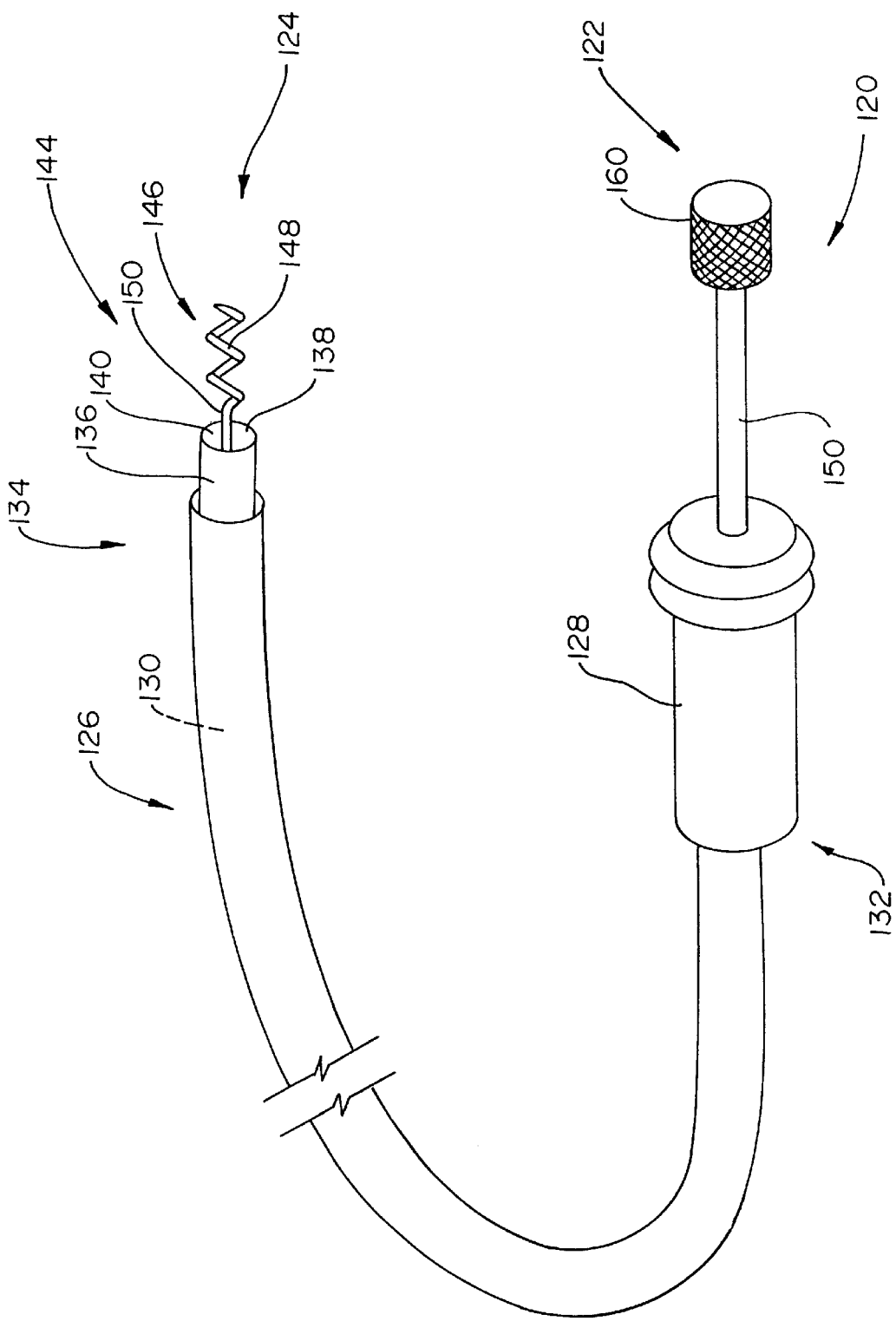
FIG. 1 is a perspective view including a therapeutic catheter and a trocar in accordance with the present invention.

FIG. 1 is a perspective view of a therapeutic catheter 120 in accordance with the present invention. In the embodiment of FIG. 1, therapeutic catheter 120 includes a distal end 124, a proximal end 122, and an elongate shaft 126 defining a lumen 130. A hub 128 is disposed about elongate shaft 126 proximate a proximal end 132 thereof. A cutter 136 is fixed to elongate shaft 126 proximate a distal end 134 thereof. Cutter 136 includes a distal edge 138 and a cutter lumen 140.

Therapeutic catheter 120 also includes a mooring member 146 disposed at a distal end of 144 of a mooring shaft 150. In the embodiment of FIG. 1, mooring member 146 includes a helix 148. Mooring shaft 150 is slidingly disposed within lumen 130 of elongate shaft 126 and cutter lumen 140 of cutter 136. A knob 160 is fixed to a proximal end 122 of mooring shaft 150. In a preferred embodiment, knob 160 is adapted to be rotated by the fingers of a physician. In this preferred embodiment, the rotary motion of knob 160 is transferred to mooring member 146 via mooring shaft 150.

In a preferred embodiment, mooring member 146 and mooring shaft 150 are comprised of a metallic wire. Metals that may be suitable in some applications include stainless steel and nickel titanium alloy. It is to be appreciated that other metallic and non-metallic materials may be utilized without deviating from the spirit and scope of the present invention.

It will also be appreciated that elongate shaft 126 may be comprised of many materials without deviating from the spirit and scope of the present invention. In a preferred embodiment, elongate shaft 126 is comprised of polyether block amide (PEBA). Polyether block amide is commercially available from Atochem Polymers of Birdsboro, Pennsylvania under the trade name PEBAX. Also in a preferred embodiment, elongate shaft 126 is fabricated using an extrusion process.

It is to be understood that other manufacturing processes can be used without departing from the spirit and scope of the present invention. Elongate shaft 126 may also be comprised of other materials without departing from the spirit of scope of this invention. Examples of materials that may be suitable in some applications include: polyethylene (PE), polypropylene (PP), polyvinylchloride (PVC), polyurethane, and polytetrafluoroethylene (PTFE). Elongate shaft 126 may also include a reinforcement member. Examples of reinforcement members that may be suitable in some applications include a plurality of strands disposed in a braided pattern, a plurality of fibers knitted together, and a coiled wire.

Therapeutic catheter 120 may include one or more radiopaque markers. One example of a radiopaque marker is a band of radiopaque material disposed proximate the distal end of therapeutic catheter 120. Radiopaque bands of this type aid the physician in determining the location of the distal end of the device relative to the patient's anatomy. The radiopaque band may be comprised of a number of materials. Examples of materials that may be suitable in some applications include gold, platinum, tungsten, iron, silver, and thermoplastic material loaded with a radiopaque filler. Examples of radiopaque filler that may be suitable in some applications include barium sulfate, bismuth subcarbonate, bismuth trioxide, bismuth oxychloride, bismuth subcarbonate, tungsten powder, and depleted uranium.

Cutter 136 of therapeutic catheter 120 may be comprised of a variety of metallic and non-metallic materials. Examples of metallic materials that may be suitable in some applications include stainless steel, and nickel-titainium alloy. Examples of non-metallic materials that may be suitable in some applications include polycarbonate, polyacrylate, polyimide, and polyamide. Cutter 136 may be fixed to elongate shaft 126 using any suitable method. Examples of methods that may be suitable in some applications include welding, adhesive bonding, and mechanical coupling.

Figure 2:
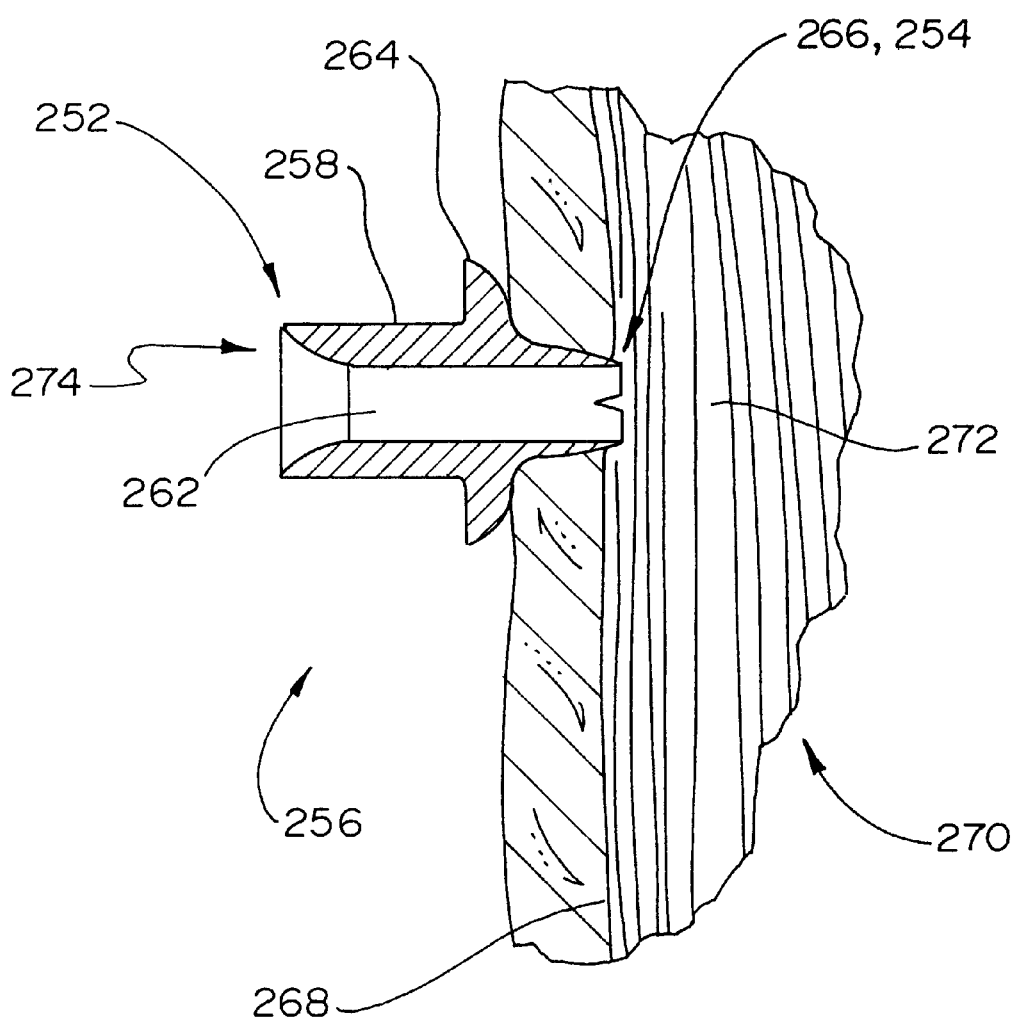
FIG. 2 is a cross-sectional view of a trocar utilized to access a muscle within a donor site in a method in accordance with the present invention.

FIG. 2 is a cross-sectional view of a trocar 256 disposed proximate a donor site 270. Trocar 256 includes a body 258 defining a trocar lumen 262. Body 258 includes a flange 264, a penetrating portion 266, a distal end 254, and a proximal end 252. In FIG. 2, penetrating portion 266 of body 258 of trocar 256 has penetrated a skin 268 of a human body proximate donor site 270. As shown in FIG. 2, a distal end 254 of trocar 256 is disposed proximate a muscle 272 of donor site 270. A proximal aperture 274 of trocar 256 is in fluid communication with trocar lumen 262. In a preferred embodiment, trocar lumen 262 of trocar 256 is adapted to receive therapeutic catheter 120. In a preferred method in accordance with the present invention, distal end 124 of therapeutic catheter 120 is inserted into trocar lumen 262 through proximal aperture 274.

Figure 3:
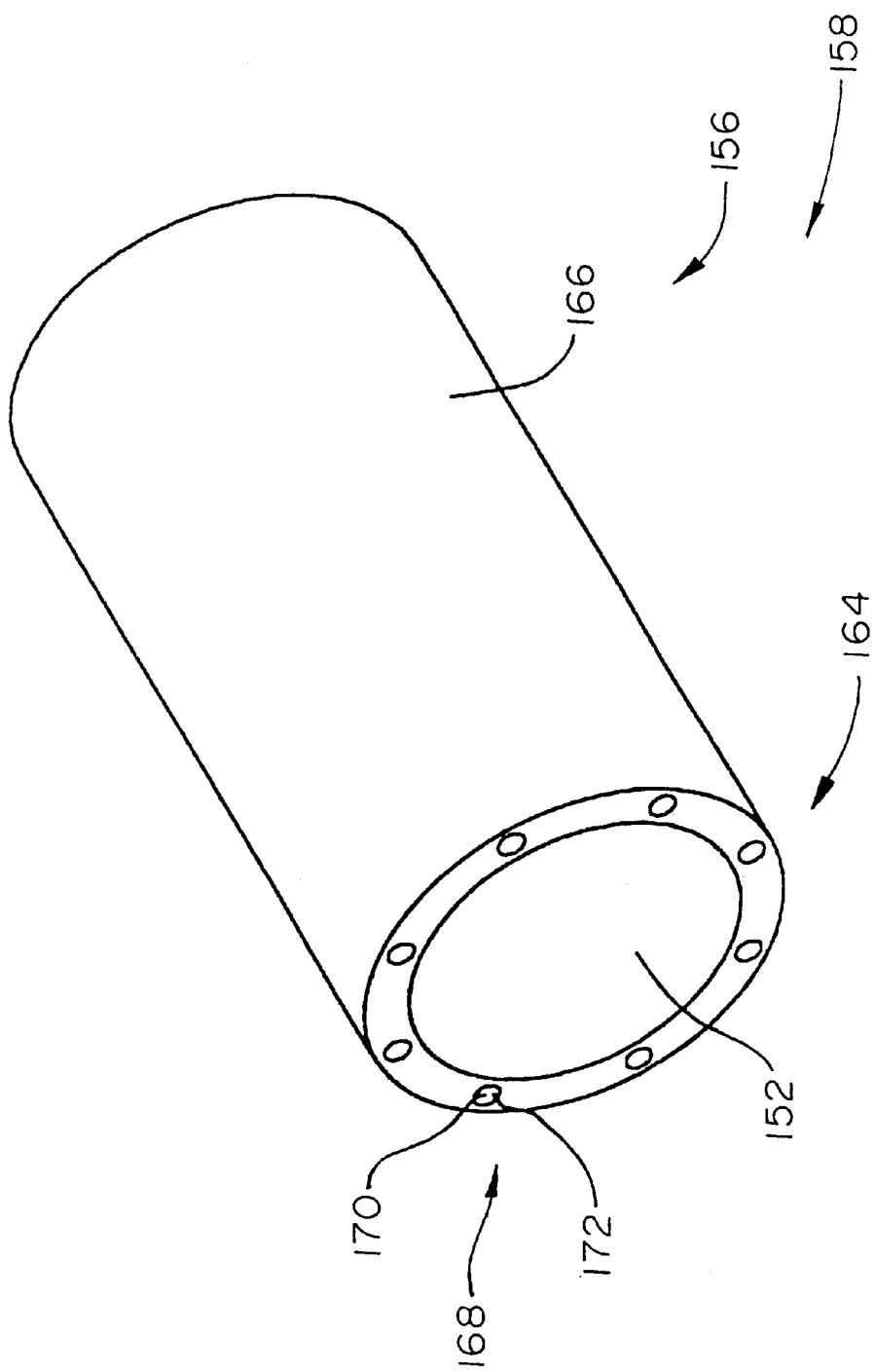
FIG. 3 is a perspective view of the distal portion of a guide catheter in accordance with the present invention.

FIG. 3 is a perspective view of a distal portion 156 of a guide catheter 158 in accordance with the present invention. Guide catheter 158 includes an elongate tubular member 166 defining a central lumen 152. A plurality of moorings 168 are disposed proximate a distal end 164 of guide catheter 158. In one method in accordance with the present invention, moorings 168 may be utilized to retain distal end 164 of guide catheter 158 proximate a donee site. In the embodiment of FIG. 3, each mooring 168 comprises a vacuum orifice 172. Each vacuum orifice 172 is in fluid communication with a vacuum lumen 170 defined by elongate tubular member 166.

Other embodiments of moorings 168 are possible without deviating from the spirit or scope of the present invention. For example, each mooring 168 may be comprised of an elongate wire with a helix disposed proximate its distal end. The helical end of the elongate wire may be "threaded" into the tissue proximate the donee site by rotating the wire. Additional examples, of moorings 168 that may be appropriate in some applications include hooks and barbs.

Guide catheter 158 may be comprised of many materials without deviating from the spirit and scope of the present invention. In a preferred embodiment, guide catheter 158 is comprised of polyether block amide (PEBA). Polyether block amide is commercially available from Atochem Polymers of Birdsboro, Pennsylvania under the trade name PEBAX. Also in a preferred embodiment, guide catheter 158 is fabricated using an extrusion process.

It is to be understood that other manufacturing processes can be used without departing from the spirit and scope of the present invention. Guide catheter 158 may also be comprised of other materials without departing from the spirit of scope of this invention. Examples of materials that may be suitable in some applications include: polyethylene (PE), polypropylene (PP), polyvinylchloride (PVC), polyurethane, and polytetrafluoroethylene (PTFE). Guide catheter 158 may also include a reinforcement member. Examples of reinforcement members that may be suitable in some applications include a plurality of strands disposed in a braided pattern, a plurality of fibers knitted together, and a coiled wire.

Guide catheter 158 may include one or more radiopaque markers. One example of a radiopaque marker is a band of radiopaque material disposed proximate the distal end of guide catheter 158. Radiopaque bands of this type aid the physician in determining the location of the distal end of the device relative to the patient's anatomy. The radiopaque band may be comprised of a number of materials. Examples of materials that may be suitable in some applications include gold, platinum, tungsten, iron, silver, and thermoplastic material loaded with a radiopaque filler. Examples of radiopaque filler that may be suitable in some applications include barium sulfate, bismuth subcarbonate, bismuth trioxide, bismuth oxychloride, bismuth subcarbonate, tungsten powder, and depleted uranium.

Figure 4:
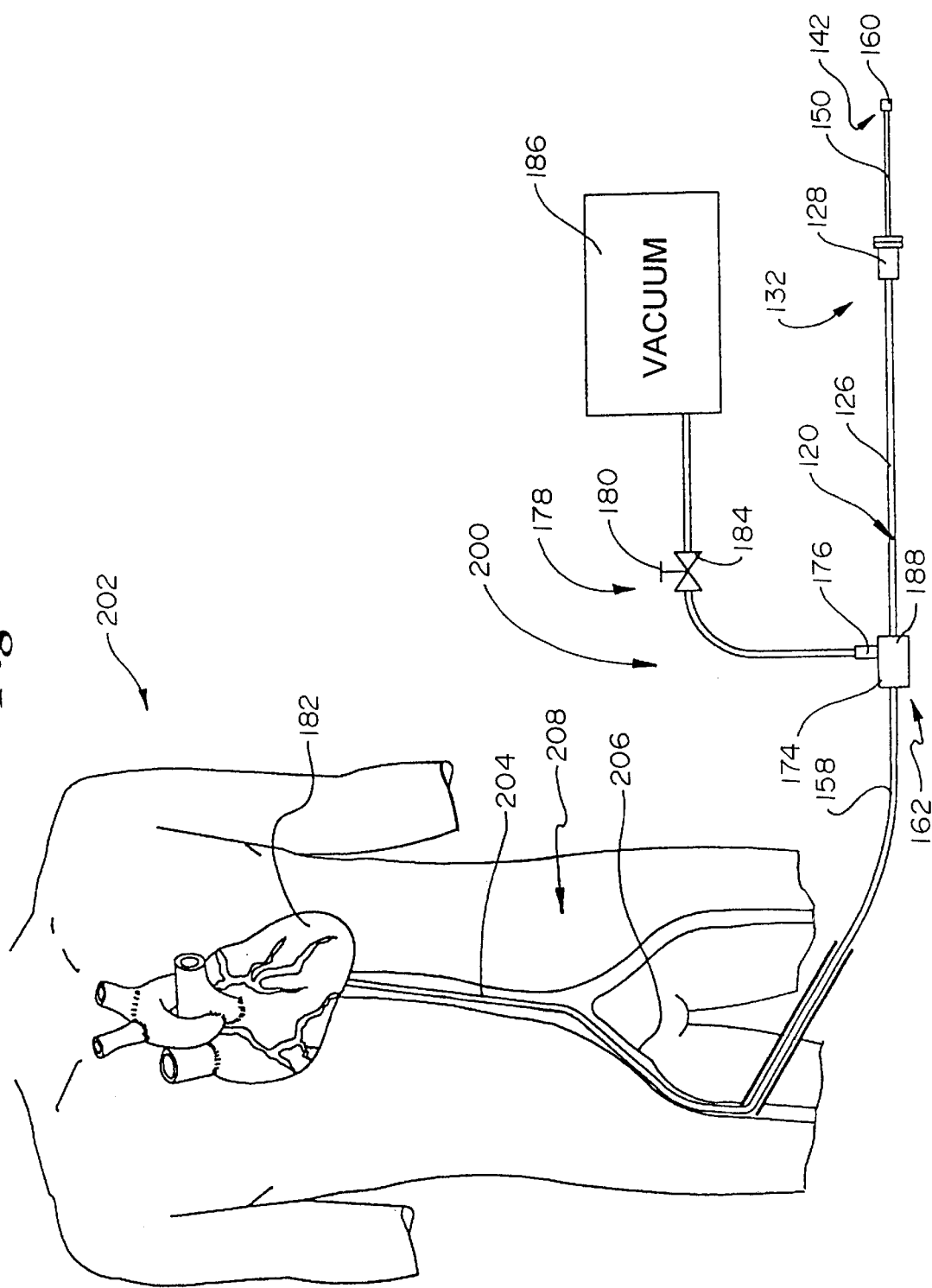
FIG. 4 is a plan view of a patient and a therapeutic catheter system in accordance with the present invention.

FIG. 4 is a plan view of a patient 202 and a therapeutic catheter system 200 including a guide catheter 158 having a central lumen and a plurality of moorings 168 (shown in FIG. 3) disposed proximate the distal end thereof. In the embodiment of FIG. 4, each mooring 168 (shown in FIG. 3) comprises a vacuum orifice 172 (shown in FIG. 3) in fluid communication with a vacuum lumen 170 (shown in FIG. 3) defined by guide catheter 158. A multi-port adapter 174 is disposed at a proximal end 162 of guide catheter 158. A vacuum port 176 of multi-port adapter 174 is in fluid communication with vacuum lumens 170 (shown in FIG. 3) of guide catheter 158.

An actuator 178 is coupled to moorings 168 (shown in FIG. 3) of guide catheter 158. In the embodiment of FIG. 4, actuator 178 includes an actuating lever 180 and a valve body 184. Valve body 184 is in fluid communication with vacuum orifices 172 (shown in FIG. 3) via vacuum port 176 of multi-port adapter 174 and vacuum lumens 170 (shown in FIG. 3) of guide catheter 158. Valve body 184 is also in fluid communication with a vacuum source 186. In the embodiment of FIG. 4, actuator 178 may selectively actuate moorings 168 (shown in FIG. 3) by selectively placing vacuum orifices 172 (shown in FIG. 3) in fluid communication with vacuum source 186.

A therapeutic catheter 120 is slidingly disposed within central lumen 152 (shown in FIG. 3) of guide catheter 158 and passes through a proximal port 188 of multi-port adapter 174. In the embodiment of FIG. 4, therapeutic catheter 120 includes an elongate shaft 126 defining a lumen 130 (shown in FIG. 1). A hub 128 is disposed about elongate shaft 126 proximate a proximal end 132 thereof. A cutter 136 (shown in FIG. 1) is fixed to elongate shaft 126 proximate a distal end 134 (shown in FIG. 1) thereof.

A mooring shaft 150 is slidingly disposed within the lumen of elongate shaft 126. A mooring member is disposed at the distal end of mooring shaft 150. A knob 160 is fixed to a proximal end 142 of mooring shaft 150. In a preferred embodiment, knob 160 is adapted to be rotated by the fingers of a physician. In this preferred embodiment, the rotary motion of knob 160 is transferred to the mooring member disposed at the distal end of mooring shaft 150.

An access catheter 204 is positioned such that its distal end is positioned within a blood vessel 206 of a vasculature 208 of patient 202. Access catheter 204 may aid in the introduction of guide catheter 158 into blood vessel 206.

In FIG. 4, distal end 164 (shown in FIG. 3) of guide catheter 158 is positioned within a heart muscle 182 of patient 202. Distal end 164 (shown in FIG. 3) of guide catheter 158 is fixed to heart muscle 182 by moorings 168(shown in FIG. 3).

Having thus described FIG. 1 through FIG. 4, methods in accordance with the present invention may now be described with reference thereto. It should be understood that steps may be omitted from these processes and/or the order of the steps may be changed without deviating from the spirit or scope of the invention. It is anticipated that in some applications, two or more steps may be performed more or less simultaneously to promote efficiency.

A method in accordance with the present invention may include the step of penetrating the skin of a patient with a trocar near a donor site. In a preferred method, the donor site includes muscle tissue. Examples of donor sites that may be suitable in some applications include arms and legs.

The distal end of a therapeutic catheter in accordance with the present invention may be inserted through a proximal orifice of the trocar. The therapeutic catheter may be urged forward through a lumen of the therapeutic catheter until a cutter of the therapeutic catheter contacts muscle tissue proximate the donor site. The mooring shaft may be urged forward within the lumen of the therapeutic catheter by applying a pushing force to the knob disposed at the proximal end of the mooring shaft. The mooring shaft may be urged forward until the mooring member of the therapeutic catheter contacts the muscle tissue of the donor site. The mooring member of the therapeutic catheter may be coupled to the muscle tissue of the donor site. In a preferred method, the mooring member is fixed to the muscle tissue by threading it into the tissue. In this preferred method, the mooring member may be rotated by applying a rotational force to the knob fixed to the proximal end of the mooring shaft.

A tendril of muscle tissue may be cut from the donor site. In a preferred method, the step of cutting the muscle tendril includes the step of urging a cutter into the muscle tissue of the donor site. The therapeutic catheter may be withdrawn from the donor site with the tendril of muscle tissue disposed within the cutter lumen.

Methods in accordance with the present invention have been envisioned in which a pulling force is applied to the knob disposed at the end of the mooring shaft. The step of pulling on the mooring shaft may be utilized to urge the muscle tendril proximally. Methods in accordance with the present invention have been envisioned in which one or more muscle tendrils are pulled into the lumen of the therapeutic catheter.

A guide catheter may be introduced into the vasculature of the patient. The guide catheter is urged forward until its distal tip is proximate a desired donee site. In a preferred method, the distal tip is urged forward until it is disposed within the heart of the patient.

Once the distal end of the sheath is positioned proximate a desired donee site, the guide catheter may be advanced so that its distal end contacts the tissue proximate the donee site. The moorings of the guide catheter may then be activated to stabilize the distal end of the guide catheter. In one embodiment of the present invention, each mooring comprises of a vacuum orifice in fluid communication with a vacuum lumen. In one method in accordance with the present invention, the moorings of the guide catheter are activated by applying vacuum from a vacuum source to the vacuum orifices via the vacuum lumens.

A pit or channel may be created in the tissue of the donee site proximate the distal end of the guide catheter. A number of methods may be utilized to create channels or pits in the tissue. Examples of methods that may be suitable in some applications include mechanical cutting and burning by exposure to electromagnetic energy. Examples of general types of electromagnetic energy that may be suitable in some applications include radio frequency energy and LASER light. A pit forming catheter may be utilized to remove material proximate the distal end of the guide catheter. A process in accordance with the present invention may include the step of inserting a pit forming catheter into the lumen of the guide catheter. The pit forming catheter may be urged forward until its distal end is proximate the distal end of the guide catheter. A pit forming member disposed proximate the distal end of the pit forming catheter may be utilized to form a pit in the tissue proximate the donee site. Examples of pit forming members that may be suitable in some applications include knives, tomes, optical fibers, and electrodes. The pit forming catheter may be withdrawn from the lumen of the guide catheter.

The distal end of a therapeutic catheter may be inserted into the proximal port of the guide catheter. The therapeutic catheter may be urged forward within the lumen of the guide catheter until the distal portion of the therapeutic catheter is disposed proximate the pit or channel in the tissue of the donee site. The muscle tendril may then be urged into the pit or channel in the tissue of the donee site. In a preferred method, the muscle tendril is urged forward by applying a pushing force on the knob fixed to the proximal end of the mooring shaft.

While the muscle tendril is disposed within the pit or channel in the tissue of the donee site, the muscle tendril may be, preferably, fixed in place with an anchor member. Various anchor members may be utilized without deviating from the spirit and scope of the present invention. Examples of anchor members include sutures, staples, cauterized areas of tissue, adhesive bonds, cork screws, wire loops, sleeves, barbs, and hooks. After the muscle tendril has been positioned in the pit or channel and preferably, anchored, the mooring member of the therapeutic catheter may be disengaged from the muscle tendril. In a preferred method, the mooring is disengaged from the muscle tendril by applying a rotational force to the knob fixed to the proximal end of the mooring shaft.

Figure 5:
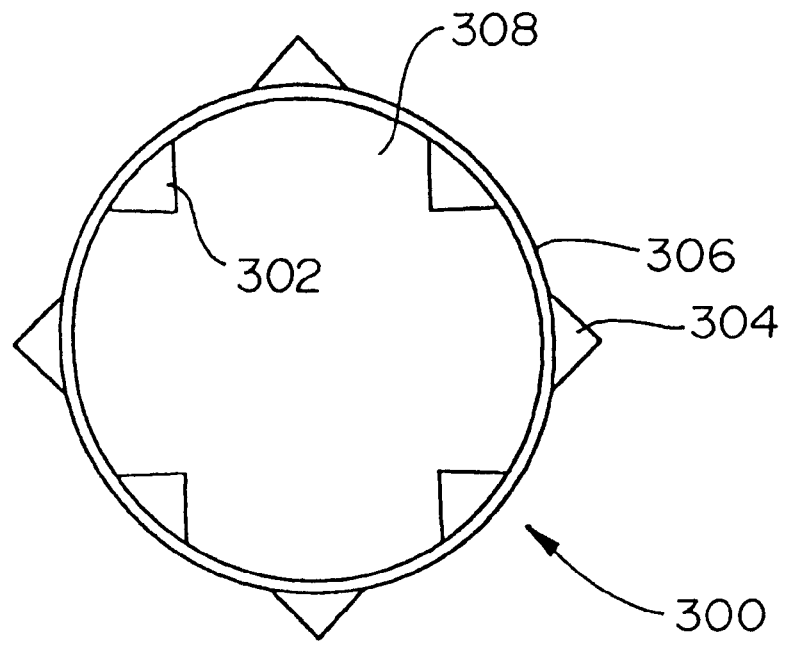
FIG. 5 is a plan view of an anchor member in accordance with an exemplary embodiment of the present invention.

FIG. 5 is a plan view of an anchor member 300 in accordance with the present invention. Anchor member 300 comprises a generally tubular frame 306 defining a lumen 308. Anchor member 300 also includes a plurality of inwardly direct barbs 302 that are directed into lumen 308, and a plurality of outwardly direct barbs 304 that are directed away from lumen 308.

Figure 6:
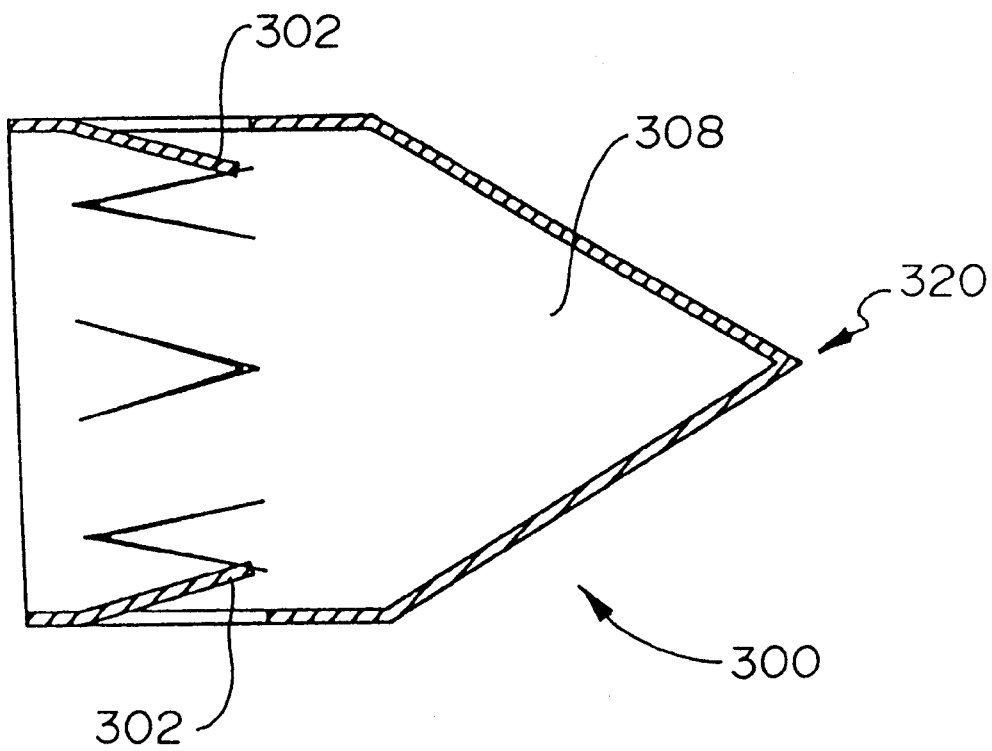
FIG. 6 is a cross-sectional view of the anchor member of FIG. 5.

FIG. 6 is a cross-sectional view of anchor member 300 of FIG. 5. In FIG. 6, it may be appreciated that anchor member 300 includes a point 320. In one method in accordance with the present invention, point 320 of anchor member 300 may be urged into the tissue of a donee site. In a particularly preferred embodiment, point 320 of anchor member 300 may be urged into the tissue of a donee site without the prior step of creating a pit or channel in the tissue. In FIG. 6, inwardly direct barbs 302 can be seen protruding into lumen 308 of anchor member 300. In a method in accordance with the present invention, an end portion a muscle tendril may be inserted into lumen 308, and inwardly direct barbs 302 may assist in retaining the end portion of the muscle tendril within lumen 308.

Figure 7:
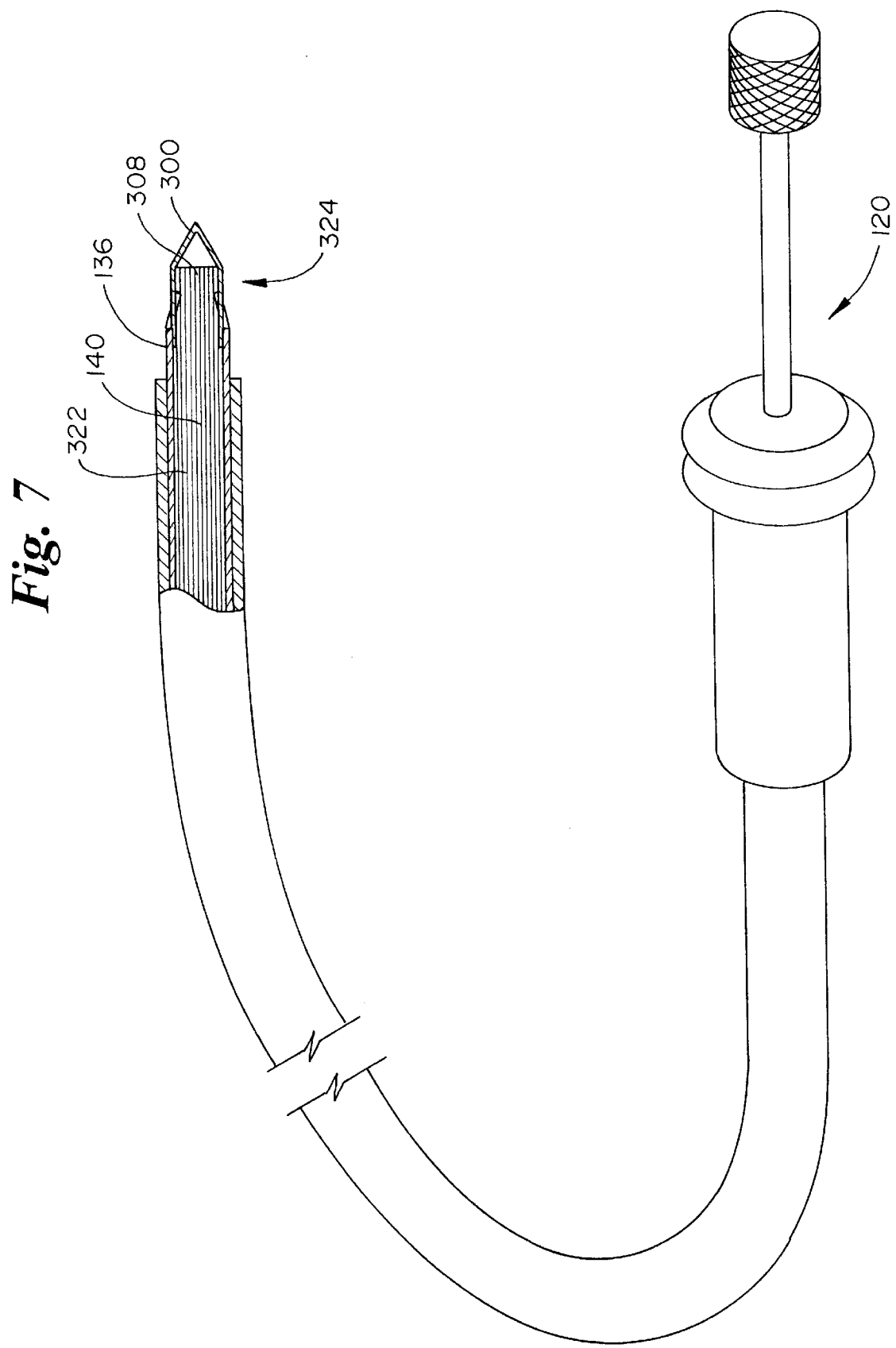
FIG. 7 is a partial cross sectional view of the catheter of FIG. 1.
Figure 8:
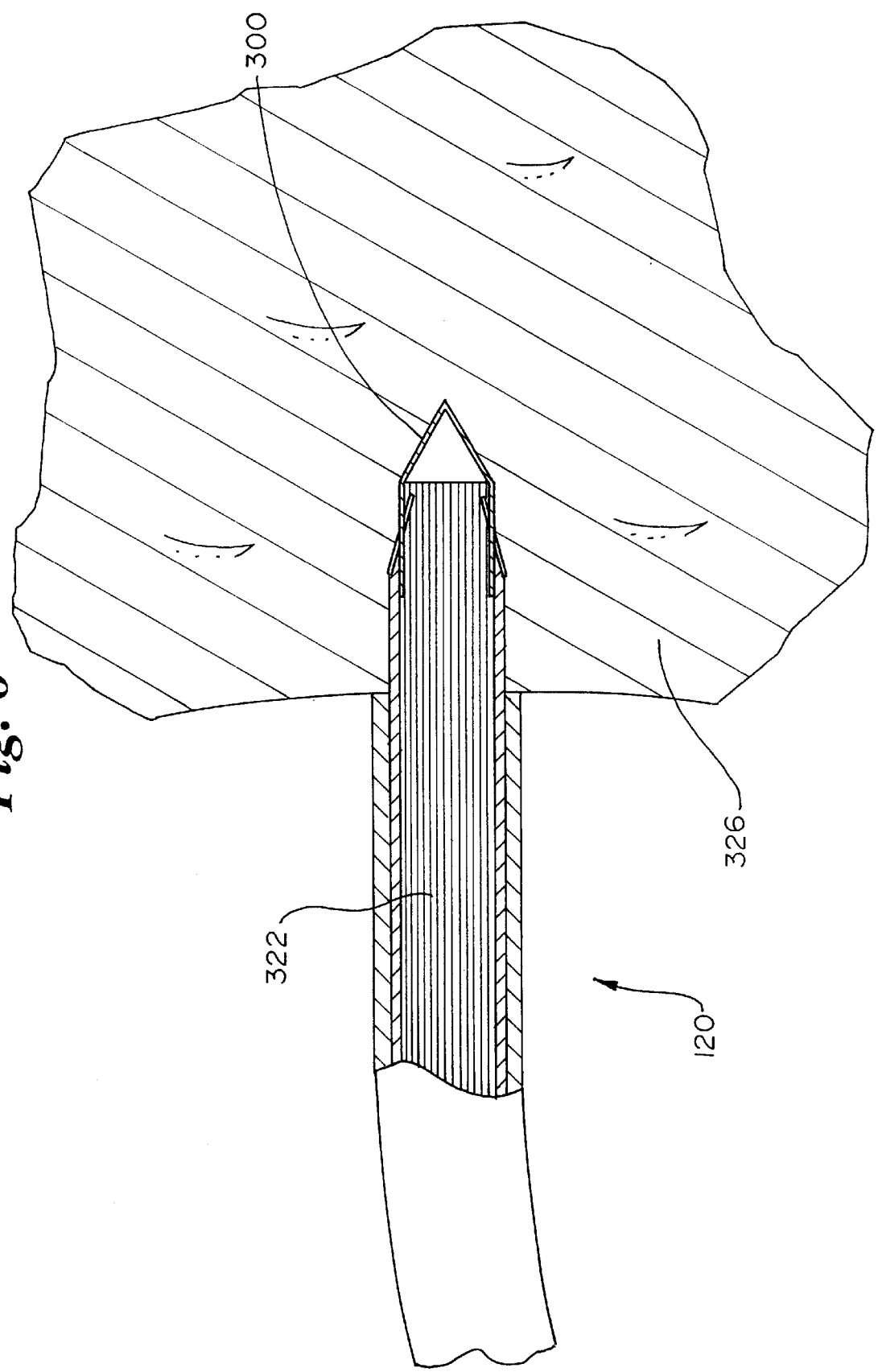
FIG. 8 is a partial cross sectional view of a distal portion of the catheter in FIG. 7.

FIG. 7 is a partial cross sectional view of catheter 120 of FIG. 1. In the embodiment of FIG. 7, a muscle tendril 322 is partially disposed within cutter lumen 140 of cutter 136. A first end portion 324 of muscle tendril 322 is disposed within lumen 308 of anchor member 300. FIG. 8 is a partial cross sectional view of a distal portion of catheter 120. In the embodiment of FIG. 8, muscle tendril 322 and anchor member 300 have been urged into a donee tissue 326.

Figure 9:
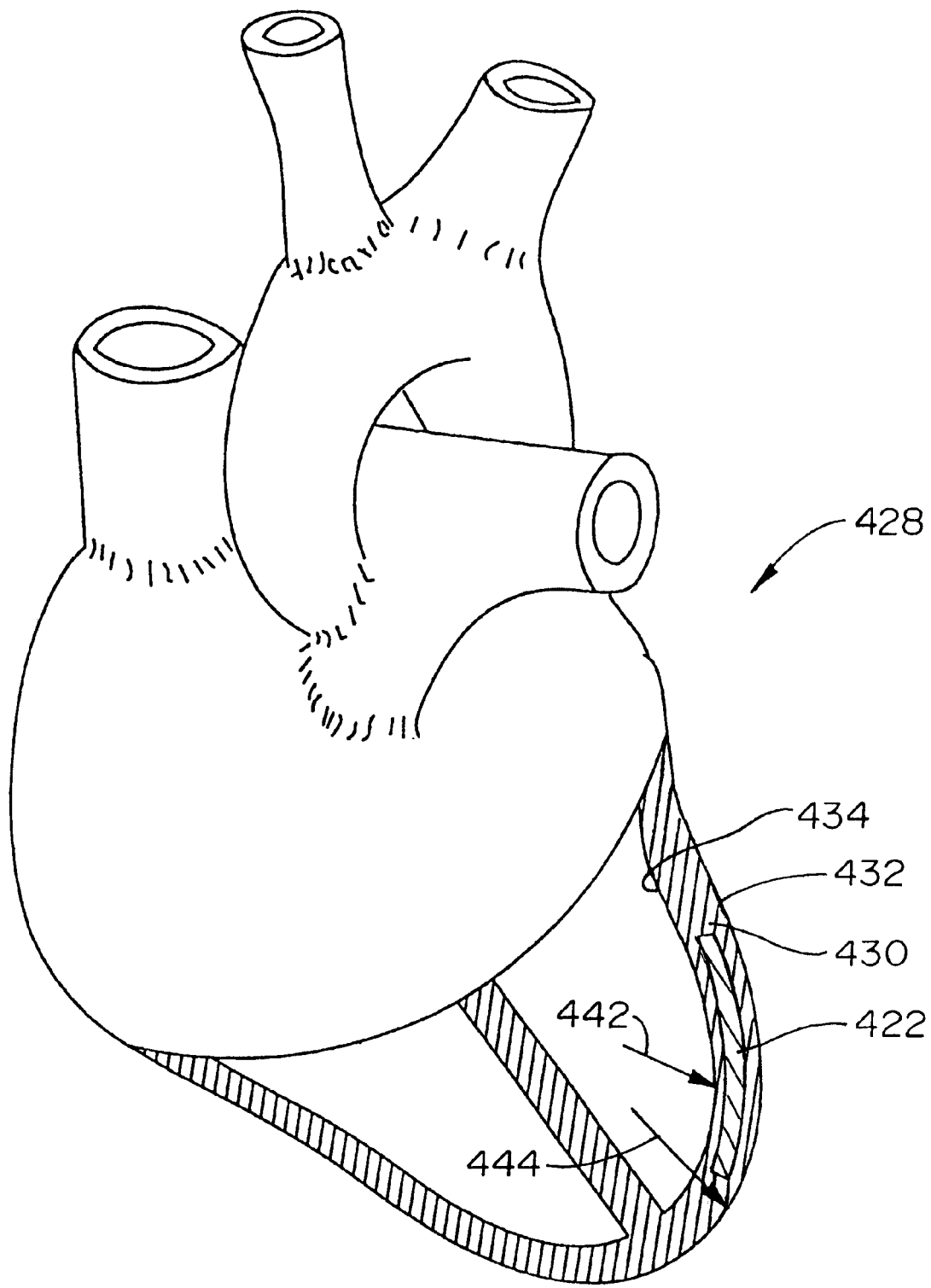
FIG. 9 is a cross sectional view of a heart and a muscle tendril disposed within a heart wall of the heart.

FIG. 9 is a cross sectional view of a heart 428 and a muscle tendril 422 disposed within a heart wall 430 of heart 428. Heart wall 430 has an outer surface 432 and an inner surface 434. In a useful embodiment, muscle tendril 422 is disposed between inner surface 434 and outer surface 432. In a preferred embodiment, muscle tendril 422 disposed so that the longitudinal axis of muscle tendril 422 is generally concentric with outer surface 432 of heart 428. In a particularly preferred embodiment, muscle tendril 422 disposed so that the longitudinal axis of muscle tendril 422 is generally concentric with outer surface 432 and inner surface 434 of heart 428. In FIG. 9 it may be appreciated that muscle tendril 422 has a radius of curvature. In a particularly preferred embodiment, the radius of curvature of muscle tendril 422 is similar to the radius of curvature of heart wall 430. In a particularly preferred embodiment, the radius of curvature of muscle tendril 422 falls between an inner radius 442 of heart wall 430 and an outer radius 444 of heart wall 430.

Figure 10:
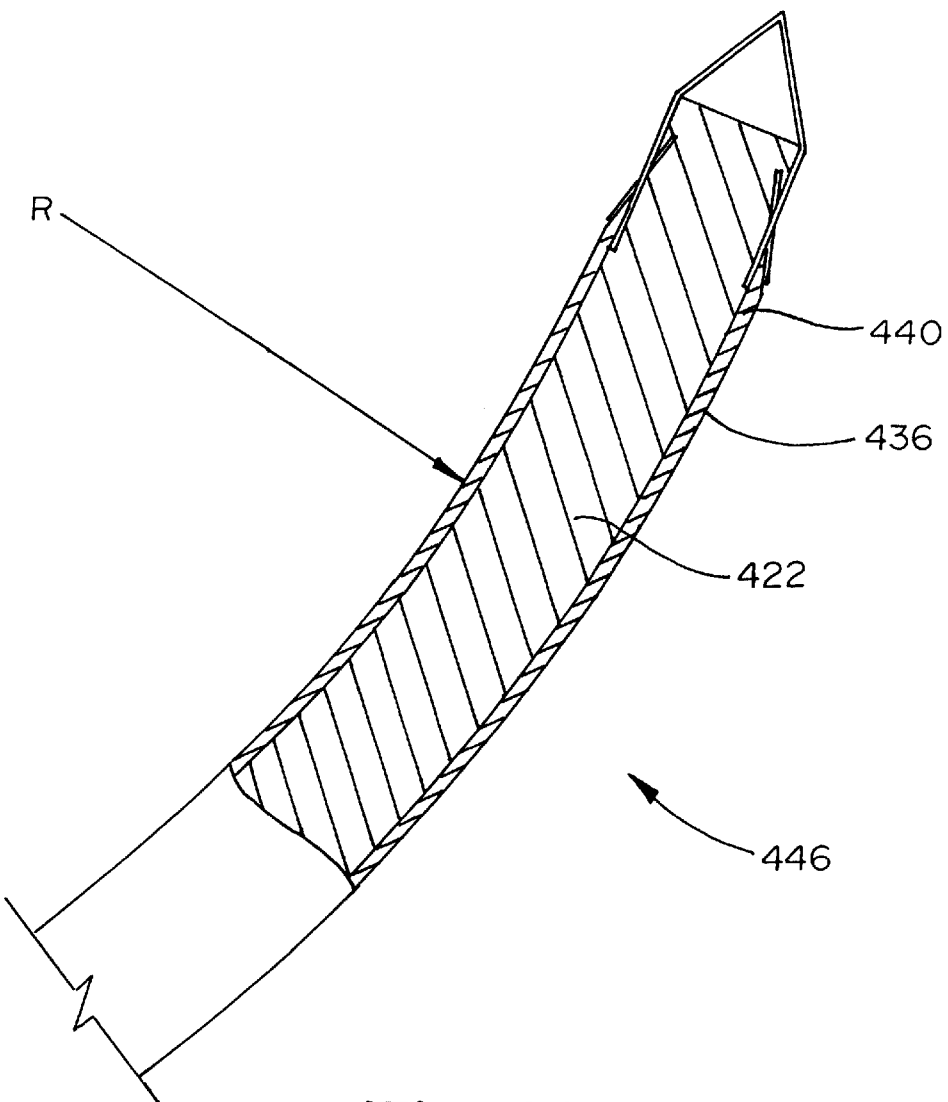
FIG. 10 is a partial cross section view of a catheter in accordance with an exemplary embodiment of the present invention.

FIG. 10 is a partial cross section view of a catheter 446 in accordance with an exemplary embodiment of the present invention. Catheter 446 includes a cutter 436 defining a cutter lumen 440. Cutter 436 is has a generally curved shape with a radius R. A muscle tendril 422 is partially disposed within cutter lumen 440. The curved shape of catheter 446 may facilitate insertion of muscle tendril 422 into heart wall 430 of heart 428, as shown in FIG. 9. In a particularly preferred embodiment, the radius of curvature of cutter 436 is similar to the radius of curvature of heart wall 430. In a particularly preferred embodiment, the radius of curvature of catheter 446 falls between inner radius 442 of heart wall 430 and outer radius 444 of heart wall 430. Although one muscle tendril is shown in FIG. 9, it is to be appreciated that a plurality of muscle tendrils may be, preferably, inserted into heart wall 430 of heart 428.

Figure 11:
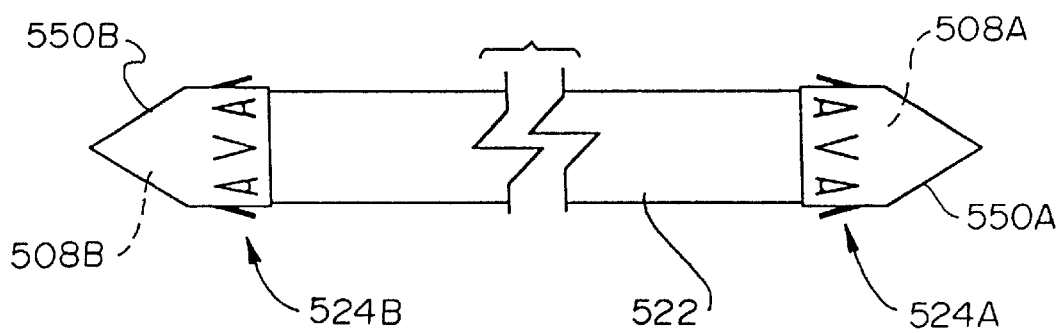
FIG. 11 is a plan view of a muscle tendril having a first end portion disposed within a first lumen of a first anchor and a second end portion disposed within a second lumen of a second anchor.

FIG. 11 is a plan view of a muscle tendril 522 having a first end portion 524A and a second end portion 524B. In the embodiment of FIG. 11, first end portion 524A of muscle tendril 522 is disposed within a first lumen 508A of a first anchor 550A and second end portion 524B of muscle tendril 522 is disposed within a second lumen 508B of a second anchor 550B.

Figure 12:
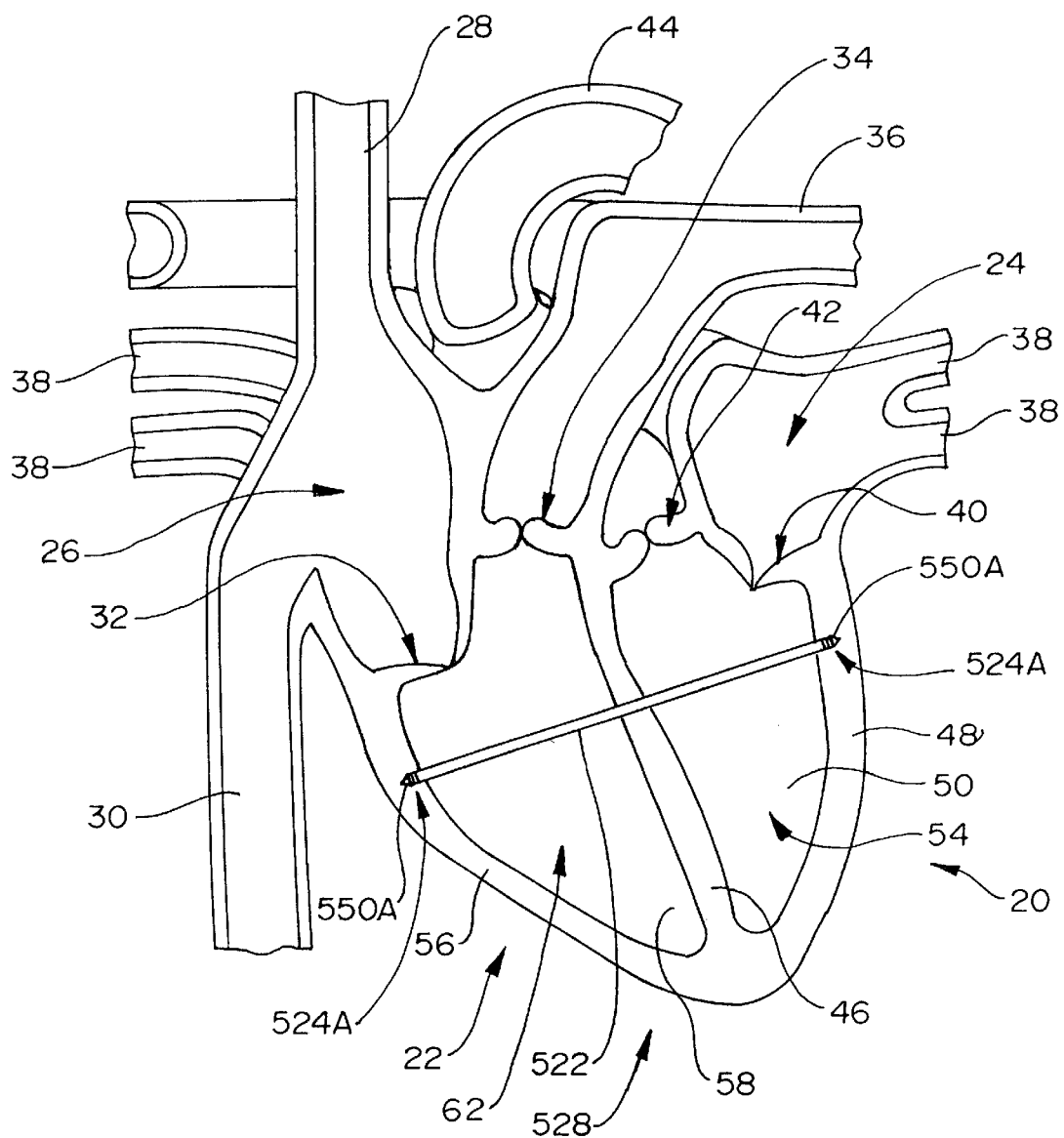
FIG. 12 is a plan view of muscle tendril that is disposed within a heart which is shown in cross section.

FIG. 12 is a plan view of muscle tendril 522 of FIG. 11. In FIG. 12, muscle tendril 522 is disposed within a heart 528 which is shown in cross section. Heart 528 includes a left ventricle 20, a right ventricle 22, a left atrium 24, and a right atrium 26. In a preferred embodiment, muscle tendril 522 aids the life sustaining blood pumping action of heart 528. During this blood pumping action, blood from the upper portion of the body flows into right atrium 26 via the superior vena cava 28. Blood from the lower portion of the body flows into the right atrium 26 via the inferior vena cava 30. A tricuspid valve 32 is in fluid communication with both the right atrium 26 and the right ventricle 22. When tricuspid valve 32 opens, it allows blood to flow from right atrium 26 into right ventricle 22. During each heart beat, tricuspid valve 32 closes and right ventricle 22 contracts, pumping blood through the pulmonary valve 34 into the pulmonary artery 36. The pulmonary artery carries blood to the lungs of the patient.

After becoming oxygenated in the lungs, blood returns to the heart via a plurality of pulmonary veins 38 which are each in fluid communication with the left atrium 24. A mitrial valve 40 is in fluid communication with both left atrium 24 and left ventricle 20. Blood returning from the lungs via pulmonary veins 38 may pass through mitrial valve 40 into left ventricle 20. During each heart beat, mitrial valve 40 closes and left ventricle 20 contracts, pumping blood through an aortic valve 42 and into the aorta 44. After passing through the aorta 44, oxygenated blood is distributed throughout the body of the patient.

The walls of a diseased heart may include areas of non-contracting tissue that may interfere with the life sustaining blood pumping action of heart 528. An area of non-contracting tissue may comprise a myocardial infarction, a stenosis, and etc. Areas of non-contracting tissue may be caused by, for example, ischmia, which is a decreased supply of blood to an area of tissue. Non-contracting tissue may also be the result of idiopathic disease, which is a disease which develops without an apparent or known cause. Additionally, an area of non-contracting tissue may comprise an area of necrosis which is localized tissue death. An area of non-contracting tissue may also comprise tissue which is hibernating due to reduced blood flow to the effected tissue.

As shown in FIG. 12, heart 528 includes a middle heart wall 46 that is disposed between the left ventricle 20 and the right ventricle 22. Left ventricle 20 includes a left heart wall 48, a dorsal heart wall 50, and a ventral heart wall 52 (not shown). Left ventricle 20 also includes a chamber 54 defined by middle heart wall 46, left heart wall 48, dorsal heart wall 50, and ventral heart wall 52. Right ventricle 22 includes a right heart wall 56, a dorsal heart wall 58, and a ventral heart wall 60 (not shown). Right ventricle 22 also includes a chamber 62 defined by middle heart wall 46, right heart wall 56, dorsal heart wall 50, and ventral heart wall 60.

In the embodiment of FIG. 12, first anchor 550A and first end portion 524A of muscle tendril 522 are disposed within left heart wall 48 of left ventricle 20. In a similar fashion, second anchor 550B and second end portion 524B of muscle tendril 522 are disposed within right heart wall 56 of right ventricle 22. Also in the embodiment of FIG. 12, muscle tendril 522 passes through middle heart wall 46 of heart 528. In a preferred embodiment, muscle tendril 522 assists heart 528 in pumping blood. In a particularly preferred embodiment, muscle tendril 522 assists heart 528 in pumping blood by contracting when left ventricle 20 and right ventricle 22 of heart 528 contract (i.e., muscle tendril itself contracts).

Figure 13:
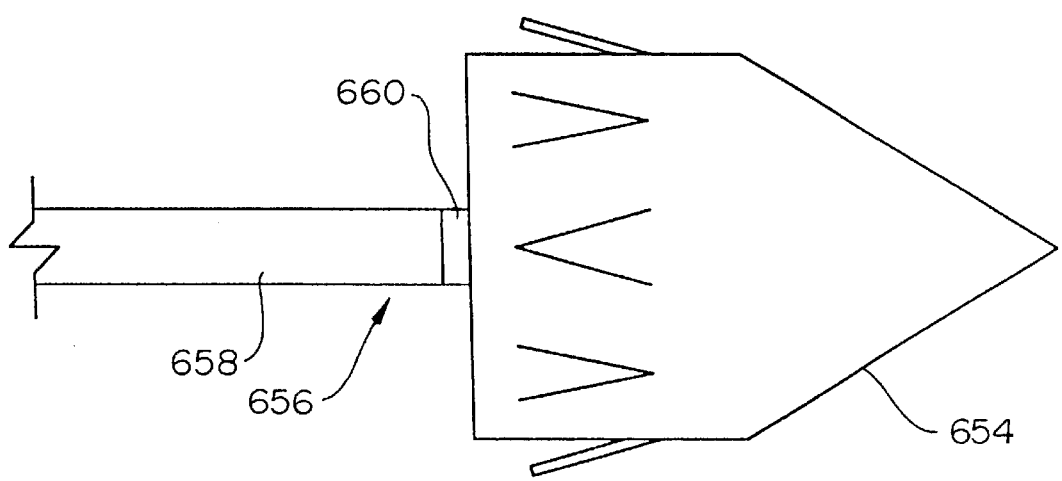
FIG. 13 is a plan view of an additional embodiment of an anchor in accordance with an exemplary embodiment of the present invention.

FIG. 13 is a plan view of an additional embodiment of an anchor 654 in accordance with the present invention. A distal end 656 of an elongate member 658 is releasably fixed to anchor 654. In the embodiment of FIG. 13, the releasable fixing of elongate member 658 to anchor 654 is accomplished utilizing a sacrificial material 660 disposed between distal end 656 of elongate member 658 and anchor 654. In a preferred embodiment, sacrificial material 660 comprises a material that may be selectively decayed via electrolytic corrosion. For example, when it is desirable to disconnect elongate member 658 from anchor 654, an electrical current may be passed through sacrificial material 660. This electrical current may cause sacrificial material 660 to corrode, dissolve, or disintegrate until the bond between elongate member 658 and anchor 654 is broken.

Figure 14:
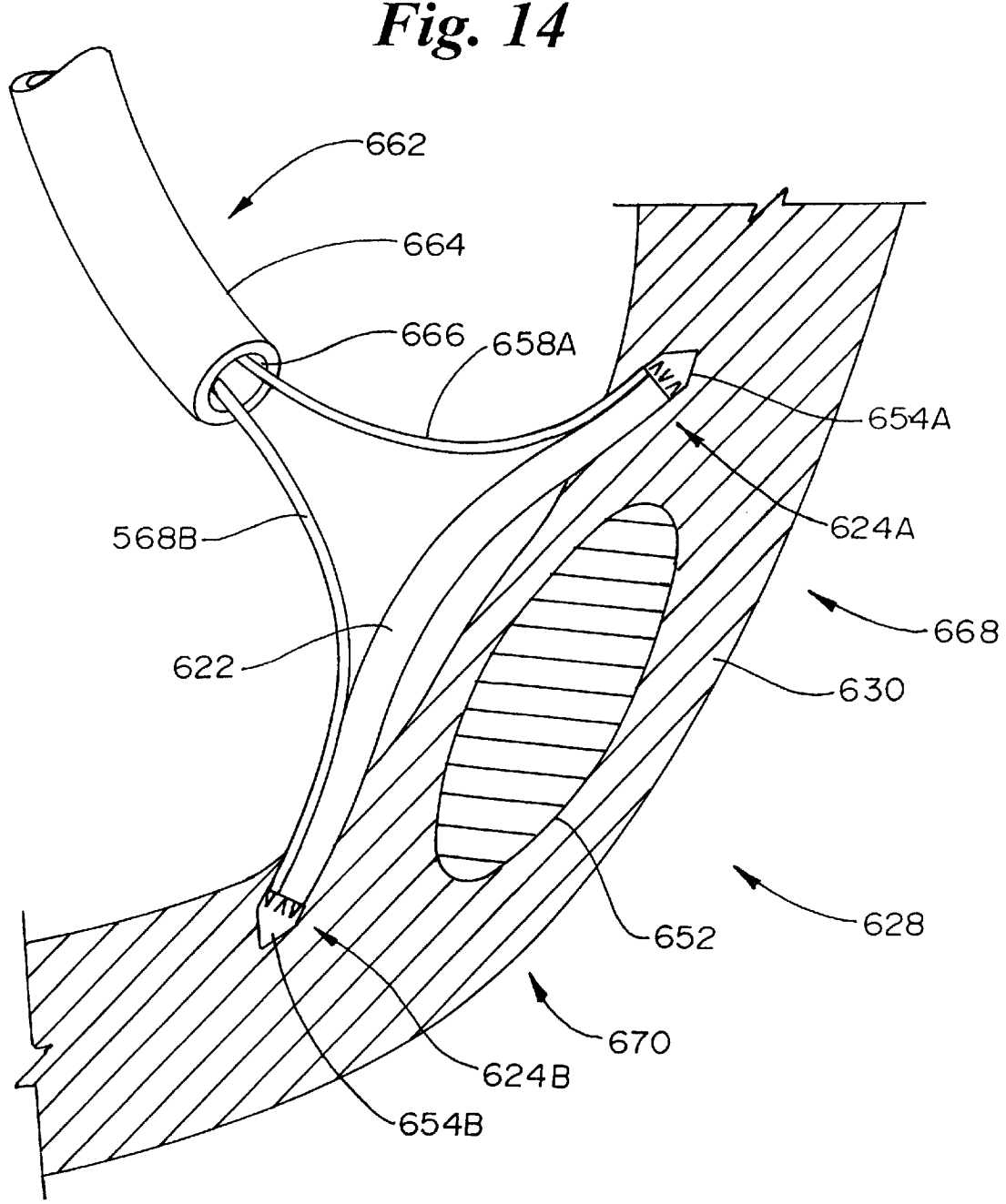
FIG. 14 is a cross sectional view of a heart wall including a localized area of non-contracting tissue 652.

FIG. 14 is a cross sectional view of a heart wall 630 of a heart 628 including a localized area of non-contracting tissue 652. Non-contracting tissue 652 may comprise a myocardial infarction, an ischmia, a stenosis, an area of necrosis, hibernating tissue, etc. An insertion catheter 662 is also illustrated in FIG. 14. In a method in accordance with the present invention, insertion catheter 662 may be utilized to treat heart wall 630. In FIG. 14, insertion catheter 662 includes a sheath 664 defining a lumen 666. A first elongate member 658A and a second elongate member 658B are both partially disposed within lumen 666 of sheath 664. First elongate member 658A has a distal end that is releasably fixed to a first anchor 654A. In a similar fashion, second elongate member 658B has a distal end that is releasably fixed to a second anchor 654B. As shown in FIG. 14, a first end portion 624A of a muscle tendril 622 is fixed to first anchor 654A, and a second end portion 624B of a muscle tendril 622 is fixed to second anchor 654B. First anchor 654A is disposed within heart wall 630 proximate a first side 668 of non-contracting tissue 652. Second anchor 654B is disposed within heart wall 630 proximate a second side 670 of non-contracting tissue 652. In a preferred embodiment, muscle tendril 622 assists heart 628 in pumping blood. In a particularly preferred embodiment, muscle tendril 622 assists heart 628 in pumping blood by contracting when heart wall 630 contracts.

Figure 15:
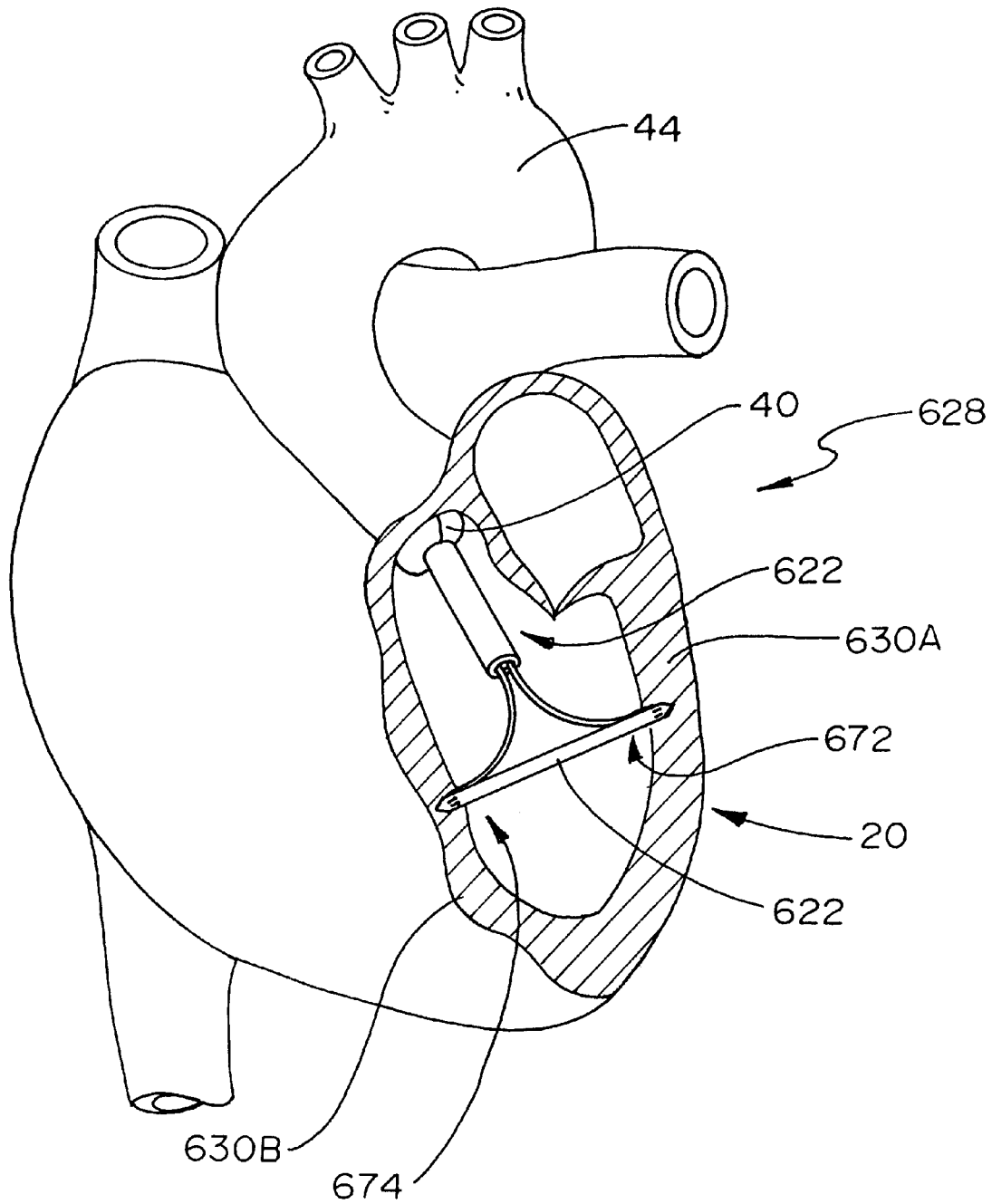
FIG. 15 is a partial cross sectional view of a heart and a muscle tendril spanning the chamber of a left ventricle of the heart.

FIG. 15 is a partial cross sectional view of a heart 628. In the embodiment of FIG. 15, a distal portion of insertion catheter 662 has been advanced through an aorta 44 and a mitrial valve 40 of heart 628. A muscle tendril 622 is disposed within a left ventricle 20 of heart 628. A first end portion 672 of muscle tendril 622 is fixed to a first heart wall 630A and a second end portion 674 of muscle tendril 622 is fixed to a second heart wall 630B.

In the embodiment of FIG. 15, muscle tendril 622 is disposed so that it spans a chamber of left ventricle 20. Embodiments of the present invention have been envisioned in which muscle tendrils span other chambers of the heart. Examples of heart chambers include the left atrium chamber, the right atrium chamber, and the right ventricle chamber. Muscle tendrils disposed in this manner may aid the blood pumping action of the heart chambers. Embodiments of the present invention have also been envisioned in which a plurality of muscle tendrils span one or more chambers of the heart.

The aforementioned embodiments of the present inventions describe muscle fibril implantations which may be caused to contract by developing electrical connections to adjacent conducting myocytes. It is also contemplated that an external electrical stimulator could be utilized to synchronously excite the muscle fibrils in a manner as to maximize the beating efficiency of the heart. A series of electrically excitable anchors is envisioned that could be connected to a muscle stimulator, similar to those devices used in cardiac myoplasty procedures.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of increasing the volume of blood pumped by a heart muscle, comprising the steps of:

providing an muscle tendril having a first end, a second end, and an intermediate portion therebetween;

disposing the muscle tendril within a chamber of the heart;

fixing a first end of the muscle tendril to the heart wall proximate a first chosen location;

fixing a second end of the muscle tendril to the heart wall proximate a second chosen location; and causing said muscle tendril to assist the heart in pumping blood.

2. The method of claim 1 wherein said muscle tendril assists the heart in pumping blood by contracting when the heart wall contracts.

3. The method of claim 2 wherein an external electrical stimulator is utilized to excite the muscle tendril.

4. The method of claim 2 wherein no external electrical stimulator is utilized to excite the muscle tendril.

5. The method of claim 4 wherein the muscle tendril is excited to contract by developing electrical connections to adjacent conducting myocytes.

6. The method of claim 2, wherein, on a heart wall having an area of non-contracting tissue, on locating the non-contracting tissue, choosing the first chosen location proximate a first end of the non-contracting tissue, and choosing the second chosen location proximate a second end of the non-contracting tissue.

7. The method of claim 2, wherein the first chosen location is on a first wall of the heart and the second chosen location is on a second wall of the heart such that an intermediate portion of the muscle tendril bridges a chamber of the heart.

8. The method of claim 7, wherein the chamber of the heart is a left ventricle.

9. The method of claim 7, wherein the chamber of the heart is a right ventricle.

10. The method of claim 7, wherein the chamber of the heart is a left atrium.

11. The method of claim 7, wherein the chamber of the heart is a right atrium.

* * * * *